United States Patent [19]

Bolduc et al.

[11] Patent Number: 4,971,067
[45] Date of Patent: Nov. 20, 1990

[54] BIOPSY INSTRUMENT WITH A DISPOSABLE CUTTING BLADE

[76] Inventors: Lee Bolduc, 6416 Gainsborough Dr., Raleigh, N.C. 27612; Ralph Richart, 216 Congers Rd., New City, N.Y. 10956

[21] Appl. No.: 190,490
[22] Filed: May 5, 1988
[51] Int. Cl.$^5$ .............................. A61B 10/00
[52] U.S. Cl. .................... 128/751; 606/170
[58] Field of Search ........... 128/749, 750, 751, 752, 128/305; 606/167, 170, 171

[56] References Cited

U.S. PATENT DOCUMENTS

| | | | |
|---|---|---|---|
| 3,964,468 | 6/1976 | Schulz | 128/751 |
| 4,522,206 | 6/1985 | Whipple | 128/752 |
| 4,569,131 | 2/1986 | Falk et al. | 128/751 |
| 4,667,684 | 5/1987 | Leigh | 128/305 |
| 4,763,669 | 8/1988 | Jaeger | 128/305 |
| 4,785,825 | 11/1988 | Romaniuk | 128/751 |

OTHER PUBLICATIONS

Arthroscopy catalog, 1984 Edition (Karl Storz of Tuttlingen, West Germany).

*Primary Examiner*—Alan Cannon
*Assistant Examiner*—Randy Shay
*Attorney, Agent, or Firm*—Kenyon & Kenyon

[57] ABSTRACT

A biopsy instrument is disclosed with a pair of blades which may be brought into an interference fit contact to generate a shearing force therebetween. The blades form an assembly which is removably attached to the instrument and is disposable. A trigger-type mechanism is provided for operating the blades. A jig is also provided for installing and removing the disposable blade assembly.

18 Claims, 6 Drawing Sheets

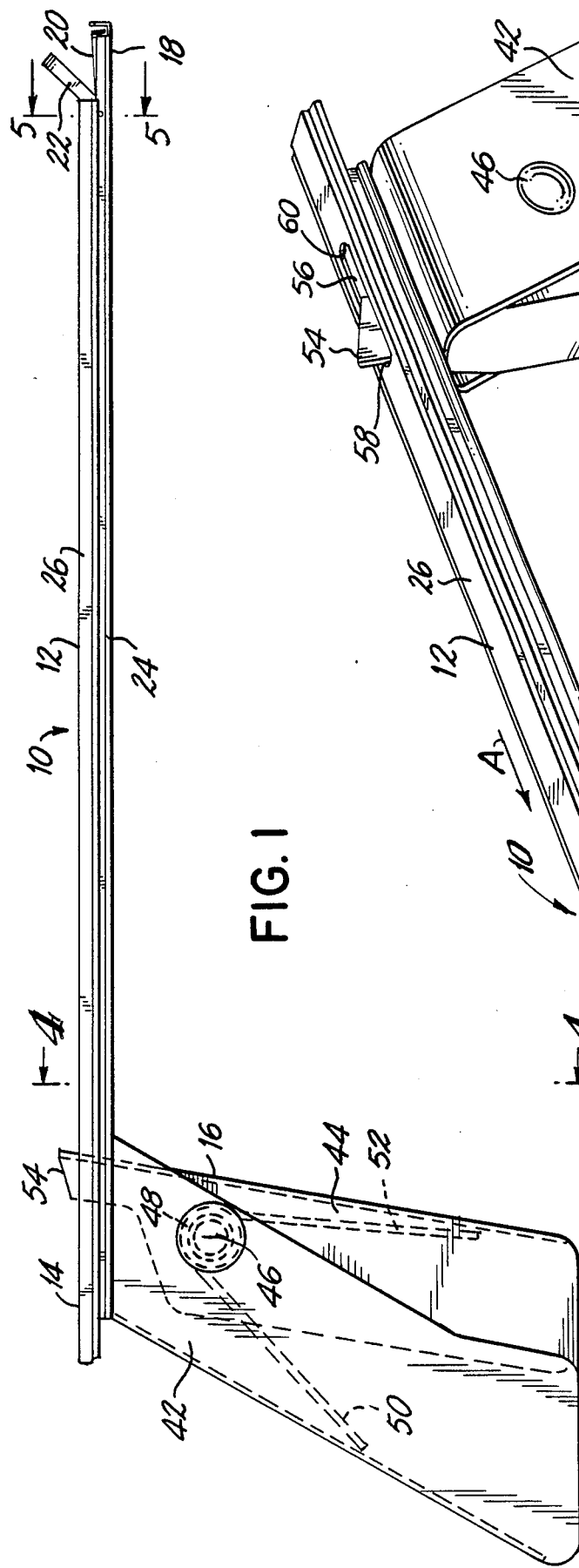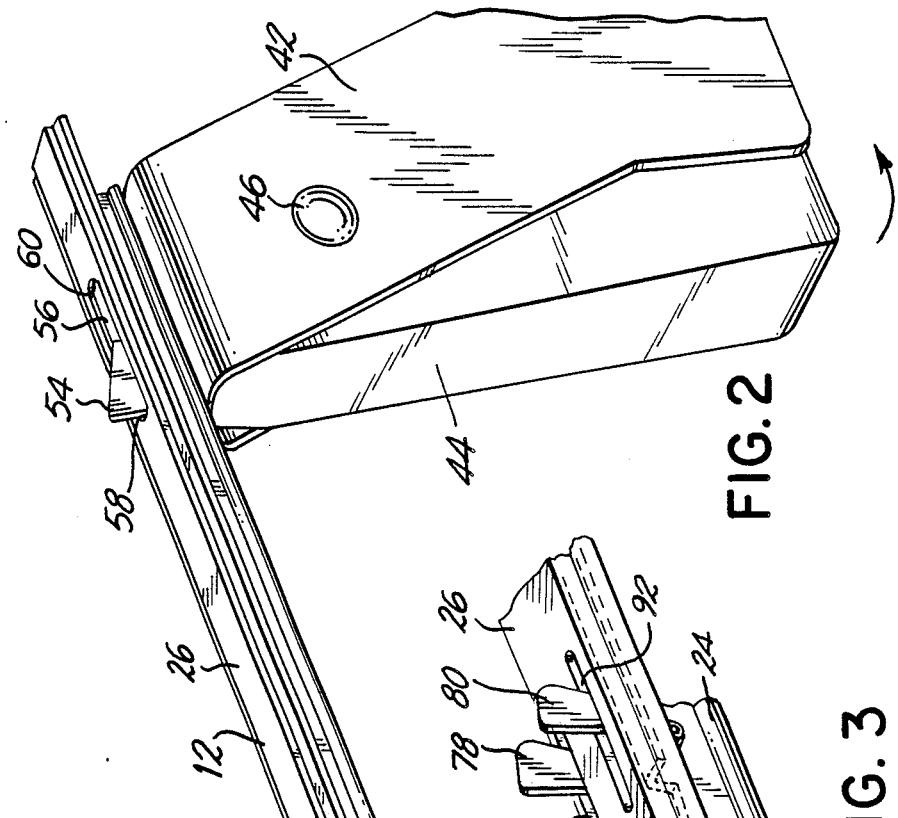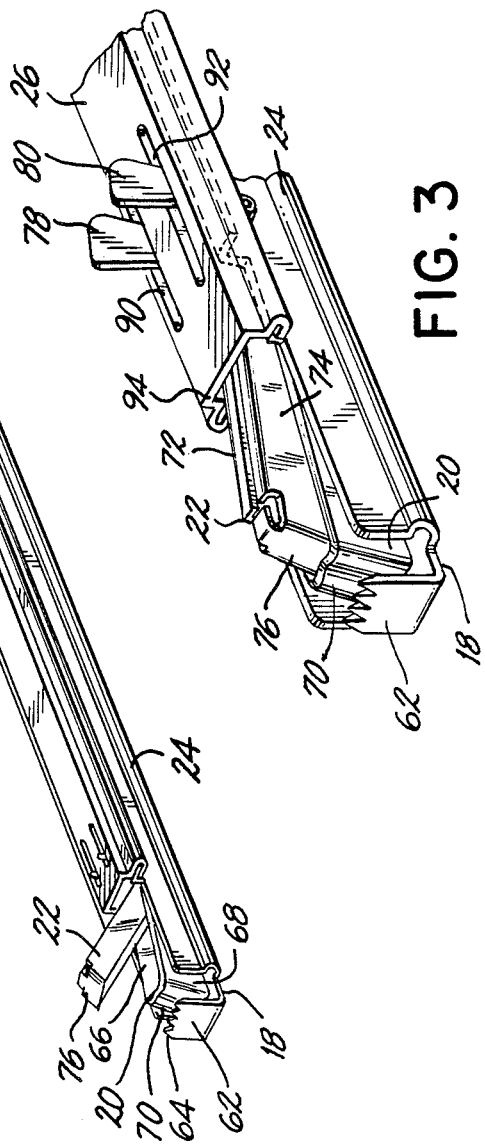

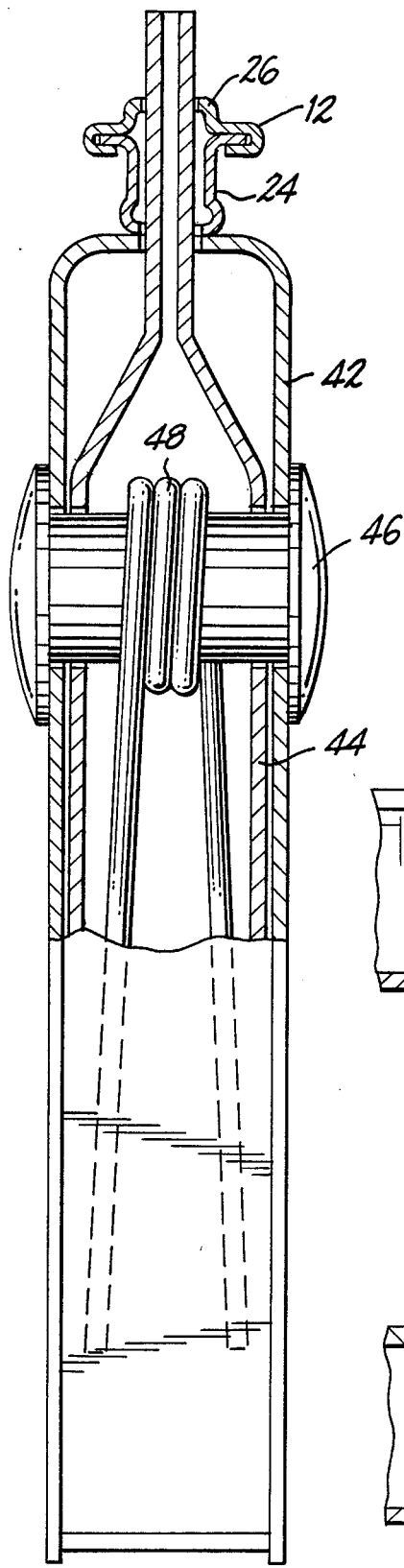
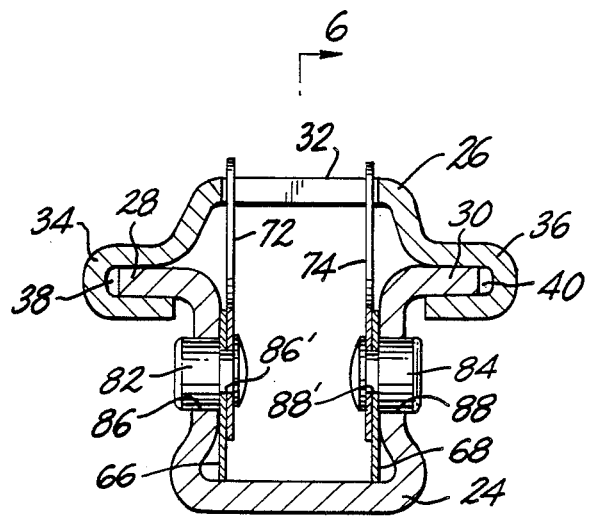
FIG. 5
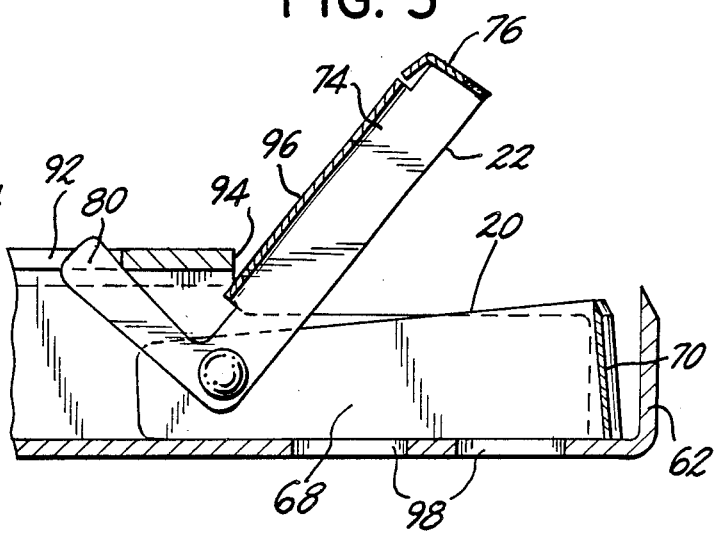
FIG. 6
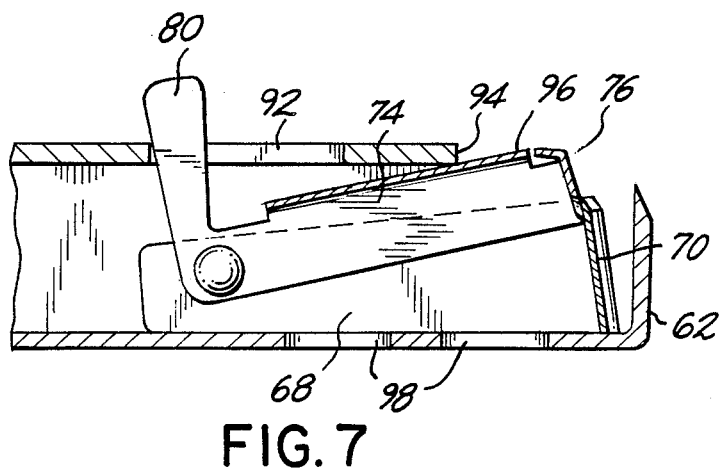
FIG. 4 FIG. 7

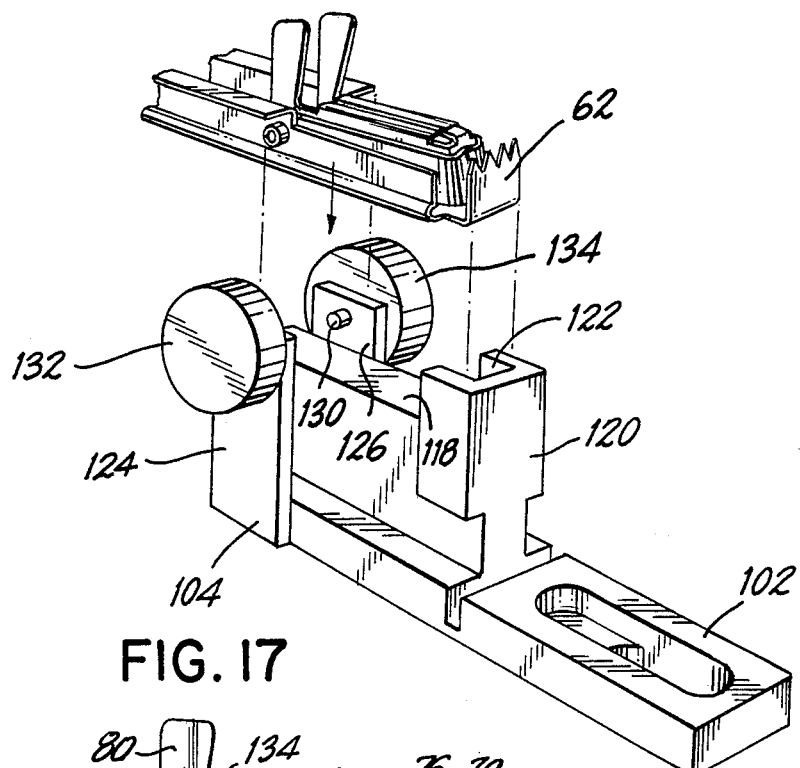
FIG. 17
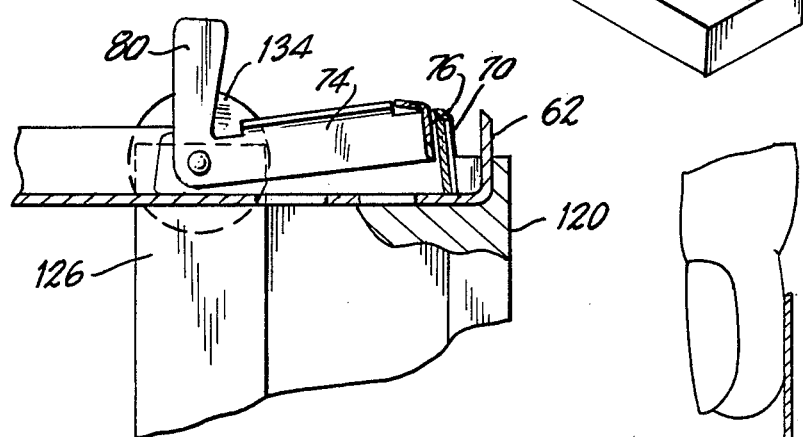
FIG. 18
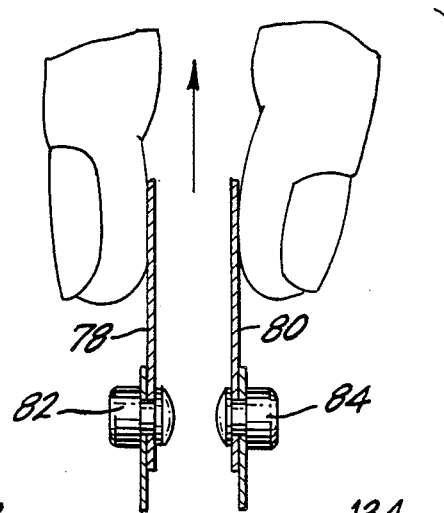
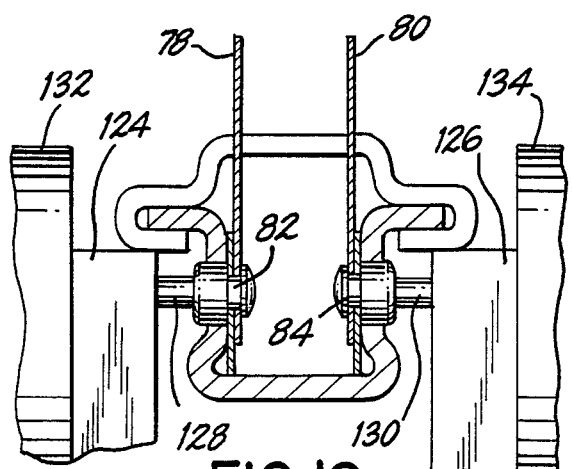
FIG. 19
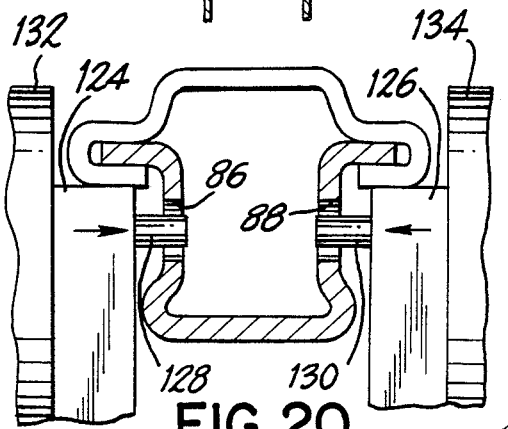
FIG. 20

BIOPSY INSTRUMENT WITH A DISPOSABLE CUTTING BLADE

BACKGROUND OF THE INVENTION

1. Field of Invention

This invention relates to a biopsy instrument having a disposable cutting blade assembly and more particularly to an instrument which may be used to sever and remove a minute portion of a cervix in vivo.

2. Description of the Prior Art

Instruments for removing tissue samples in vivo and more particularly for removing cervix samples are known in the art. One such instrument is disclosed in U.S. Pat. No. 4,243,047 to Olsen. This prior art instrument comprises an elongated arm terminating in two blades which may be pivoted toward each other in a scissor action. It is important to keep the blades sharp to insure that the sample has a clean edge. A sample cut with a dull blade may be crushed, at least partially, so that it can't be used effectively for analysis. Furthermore, using an instrument with a dull blade could cause considerable discomfort to the patient. However, the blades disclosed by Olsen are fixed, i.e., an integral part of the instrument and therefore, after several operations, they must be sharpened by hand. Manual blade sharpening is labor intensive and therefor expensive. It can cost as much as $50.00 to sharpen the blades in such instruments. A further disadvantage of the Olsen device is that the blades are activated by two handles secured at one end of the arm and which must be reciprocated like the handles of a scissor. Because of the relatively large angular motion of these handles, it is very difficult to keep the instrument and particularly its cutting end steady while closing the blades.

U.S. Pat. No. 3,943,916 to Vadas discloses another instrument for removing a cervix sample; however, this instrument takes a conical tissue sample and accordingly requires a very complex cutting mechanism.

A biopsy instrument with a replaceable blade has been available from Gyneco of Branchburg, N.J. under the name of CIN-SHEAR. However, this instrument which employs a single cutting blade has proved difficult to use and does not provide optimal cutting. Other exemplary prior art forceps and scissors are made by various instrument manufacturers such as Karl Storz of Tuttlingen, West Germany, as illustrated in its Arthroscopy catalog, 1984 Edition. However, none of these instruments have removable blades and thus must be manually sharpened.

OBJECTIVES AND SUMMARY OF THE INVENTION

In view of the above-mentioned disadvantages of the prior art devices, it is a primary objective of the present invention to provide a biopsy instrument having replaceable blade assembly so that manual sharpening of the instrument is unnecessary.

Another objective of the invention is to provide a biopsy instrument which can be held very steadily in a precise position while a sample is being cut from a body tissue.

A further objective is to provide a biopsy instrument which can be made inexpensively, for example, from a flat stainless steel sheet.

Yet another objective is to provide a simple jig for the attachment and removal of the blade assembly from the biopsy instrument. Other objectives and advantages of the invention will become apparent from the following description of the invention.

The present invention provides a biopsy instrument having an elongated member comprising two components which are slidably engaged to permit reciprocating movement of one with respect to the other. At one end of the elongated member, the cutting end, there is a removable blade assembly preferably comprising a pair of mating substantially U-shaped blades and either or both of the blades is provided with a razor sharp cutting edge. At least one of the blades may be fixed while the other is pivoted by the reciprocating movement of the components toward and away from the fixed blade. The two blades are shaped so that as they are brought together a scissor or shearing action takes place between them whereby the blades may be used to sever a clean tissue sample. The end of the elongated member opposite the cutting end is provided with a pistol grip having a trigger which may be activated by squeezing to reciprocate the components with respect to each other.

The removable blade assembly may be separated from the instrument with a special jig. The preferred jig has two sections, one section being shaped to remove the blade assembly from the instrument and the second section being shaped to insert a new replacement blade assembly in the instrument.

BRIEF DESCRIPTION OF THE FIGURES

FIG. 1 is a side view of a biopsy instrument constructed in accordance with this invention;

FIG. 2 is a perspective view of the instrument of FIG. 1;

FIG. 3 is an enlarged view of the cutting end of the instrument of FIG. 2;

FIG. 4 is a fragmentary sectional view of the biopsy instrument of FIG. 1 taken along line 4—4;

FIG. 5 is a fragmentary sectional view of the biopsy instrument of FIG. 1 taken along line 5—5;

FIG. 6 is a side sectional view of the biopsy instrument of FIG. 5 taken along line 6—6 with the movable blade in the open position;

FIG. 7 is a view similar to that of FIG. 6 with the movable blade in the closed position;

FIG. 17 is in perspective a jig positioned for removing an old blade assembly from a biopsy instrument;

FIG. 18 is a side sectional view of an old blade assembly being engaged by the jig of FIG. 12 for removal;

FIG. 19 is an end view for the jig and old blade of assembly FIG. 13; and

FIG. 20 shows the old blade assembly being removed from the biopsy instrument.

DETAILED DESCRIPTION OF THE INVENTION

Figure 8:
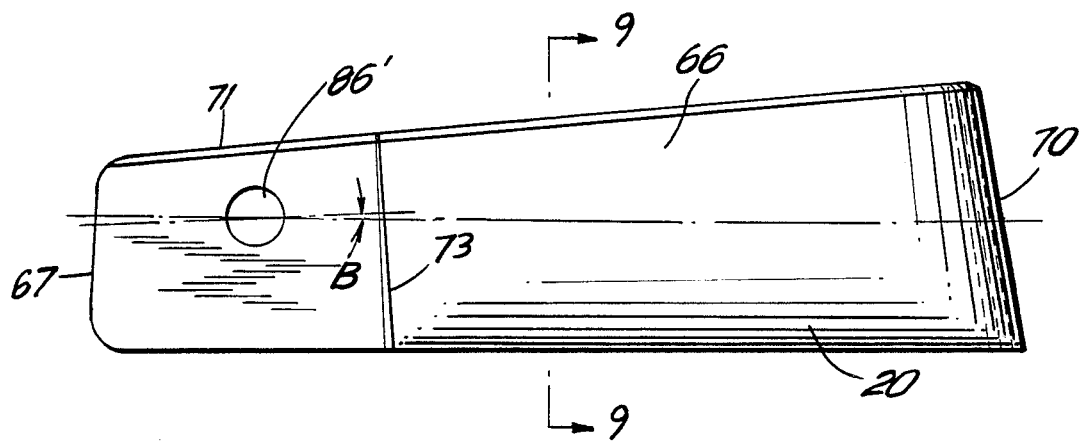
FIG. 8 shows a sides view of fixed blade, for the instrument of FIG. 1.
Figure 9:
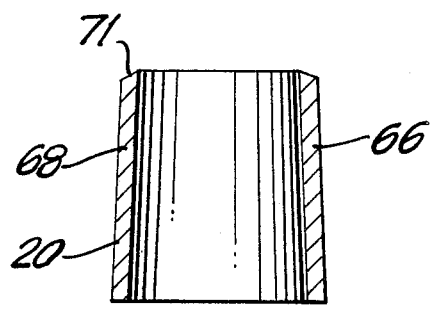
FIG. 9 shows a sectional view of the fixed blade taken along line 1X—1X in FIG. 8.

Referring now to the Figures, and more particularly to FIGS. 1-3, a biopsy instrument 10 according to this invention comprises an elongated arm 12 secured at one end 14 to a handle 16 and having a distal or cutting end 18 with a blade assembly comprising a pair of blades 20, 22 secured to the arm as described below.

Arm 12 has two essentially coextensive components 24, 26 which are attached to each other in such a manner that one may slide longitudinally with respect to the other. For example, as shown in FIG. 5, bottom component 24 may generally be U-shaped terminating in two substantially horizontal sections 28, 30. The top component may have a generally horizontal surface 32 extending between two downwardly extending side walls 34,36. Each side wall 34,36 is provided with a groove 38,40 which slideably engages the corresponding horizontal section 28,30 of the bottom component 24 in a tongue-and-groove arrangement.

Handle 16 comprises a housing 42 shaped and arranged to fit easily and comfortably in the hand. The housing is mounted on and secured to bottom component 24 of arm 12. A trigger element 44 is mounted to the housing by a pin 46. A torsion spring is mounted within the housing on pin 46 as shown in FIG. 4, and has two legs 50,52 for engaging the housing 42 and trigger element 44, respectively. Torsion spring 48 is arranged to urge trigger element 44 towards the rest position shown in FIG. 1. Trigger element 44 has an extension 54 which passes through a slot 56 in the upper component 26 of arm 12. The slot has a forward wall 58 and a rear wall 60. When the trigger element is squeezed to counteract torsion spring 48 (thereby pivoting the trigger element counterclockwise as seen in FIG. 2) extension 54 comes into contact with the front wall 58 of slot 56 to push top component 26 forward with respect to bottom component 24. The trigger and the houncing are preferably made of 304 or 308 surgical stainless steel, with all edges radiused and all surfaces being glass-bead polished.

Blades 20, 22 are arranged and constructed so that the forward movement of top component 24 causes the blades to close for severing a tissue sample. In FIG. 2 the blades are shown in the open position and in FIG. 3 the blades are closed Releasing trigger element 44 causes the top component 16 to shift back thereby returning the blades to the open (rest) position. The bottom component 24 is provided at the cutting end with a front wall 62 ending in a serrated surface 64 The purpose of this wall is to engage and hold the tissue (e.g , the cervix) while a sample is being removed therefrom.

Figure 10:
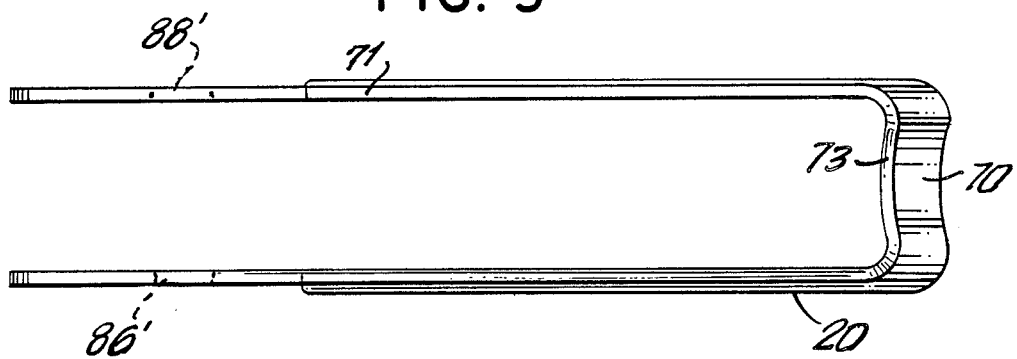
FIG. 10 shows a top view of the fixed blade of FIG. 8.

The structure of the blades 20, 22 will now be described. As shown in the FIGS. 3 and 5-10, blade 20 is generally U-shaped and comprises two substantially parallel side walls 66, 68 joined by a connecting wall 70. Blade 20 is secured to bottom component 24 by an interference fit between the blade and the component sidewalls. Preferably semicircular wall 70 is slanted as shown in FIG. 10 at an angle of about 6°.

Similarly, the side walls 66, 68 are slanted at an angle of about 2°. The top edge 71 of blade 20 is uniformly chamfered so that it slopes downard from inside at an angle of about 20°. Preferably side walls 66, 68 are slanted only between a line 73 and connecting wall 70.

The remaining sections of side walls 66, 68 surround holes 86', 88'. Side walls 66, 68 also rise upwardly from end 67 to end 70 as shown in FIG. 8 at an angle B which is preferably about 5°.

Figures 11, 12:
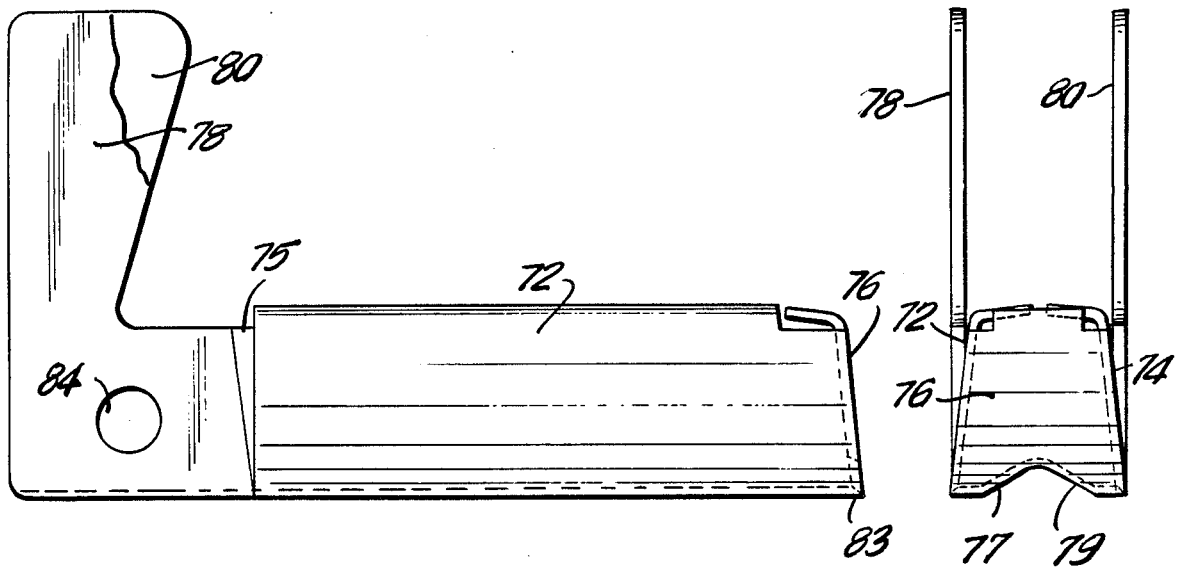
FIG. 11 shows a side view of the movable blade.
FIG. 12 shows an end view of the movable blade of FIG. 11.

Blade 22 is also U-shaped and includes two substantially parallel side walls 72, 74 joined by a connecting wall 76 as shown in FIGS. 11, 12. Side walls 72, 74 are L-shaped having two extensions 78, and 80 respectively. Each of the side walls is provided with a pin 82, 84. Between a line 75 and connecting wall 76, side wall 74 is slanted at an angle of about 6°, as shown in FIG. 12. Similarly connecting wall 76 is slanted at an angle of about 6° as shown in FIG. 11. On the bottom edge 77, connecting wall 76 is provided with a curved notch 79. Furthermore, connecting wall 76 is curved slightly inwardly as shown in FIG. 10. The bottom component 24 and blade 20 are provided with corresponding side holes 86, 88 and 86', 88' respectively for housing pins 82, 84 whereby blades 20 and 22 are pivotly attached to component 24.

The blades 20, 22 are made of a high strength, high flexibility stainless steel such as razor blade stainless steel with a thickness of about 0.004". Therefore, blades 20 and 22 are easily removed by flexing sidewalls 72, 74 toward each other until pins 82, 84 are disengaged from the corresponding holes, 86, 88.

Upper component 26 has two parallel slots 90, 92 which house and cooperatively engage extensions 78, 80, respectively.

The blades are operated as follows. As the upper component 26 is shifted forward by trigger element 44 as described above, its front edge 94 comes into contact with a top camming surface 96 of blade 22 forcing the blade 22 to pivot toward blade 20 until semicircular wall 76 slides into and contacts semicircular wall 70 in a slight interference fit. Thus walls 70 and 76 generate a shearing force for severing a sample from a tissue. This scissoring action is enhanced by the slanting side walls as described above which insure that as component 24 advanced in the direction shown by arrow A in FIG. 2, the side walls 72, 74 flex inward to form an interference fit at one shearing contact point along each of side walls. As the blades close, the shearing contact point rides the contours of the walls and meet as the two connecting walls close in. It should be appreciated that because of their slant, the side walls of the blades touch only at the shearing point. The last portion of the cutting action, i.e., along the connecting walls 70, 76 is enhanced by the curved notch 79 on connecting wall 76. As connecting walls 70, 76 close, portion 79 of wall 76 flexes slightly inwardly to compensate for the increased distance of the lower point 83 of blade 24 from pivoting pin 84. The force at the shear point can be adjusted by changing angle B shown in FIG. 8.

After the trigger element 44 is released pulling the top component back, slots 90, 92 engage extensions 78 and 80 pivoting the blade 22 back toward its open position shown in FIGS. 3 and 6. The sample may then be easily removed from the blade 22 or 20 with a toothpick or the like. Bottom component 24 is provided with holes 98 to facilitate cleaning of the instrument.

As previously mentioned, the blades 20 and 22 are removable. After several operations, these blades becomes dull. Instead of sharpening the blades, the blades are merely removed and disposed and new blades are inserted into the instrument.

The removal of the old blades and installation of the new blades may be done manually. However, if the blades are very small, this replacement operation may require a great deal of dexterity. Thus for a biopsy instrument for the cervix, blade assembly 22 may have an overall height of 0.285", a width of 0.535", with the two side walls being spaced at a distance of 0.132". In order to facilitate the replacement of the blades, a jig has been devised as follows.

Referring to FIGS. 13 to 20, jig 100 is made of a plastic material and has generally an L-shape with a first leg 102 and a second leg 104. Leg 102 is used to insert a new blade assembly into the instrument while leg 104 is used to remove an old blade assembly. As shown in FIG. 8, each blade assembly comprises a blade 20, and a blade 22 which are pivotably joined by the pins 82,84 of blade 22. Leg 104 is generally parallelipipedal and has a cavity 106 for holding the blade assembly. Cavity 106 has a generally shallow section 108 corresponding to the shape of blade bodies and a deep section 110 corresponding to extensions 78 and 80 of blade 22. Section 110 has two parallel side walls 112, 114 which are spaced closer to each other than the spacing between the extensions 78, 80. Therefore where a new blade assembly is placed into cavity 106, the two extensions are squeezed together by the side walls, to secure the blade assembly to jig 100 and to ease the insertion of the blade into the instrument.

Figure 13:
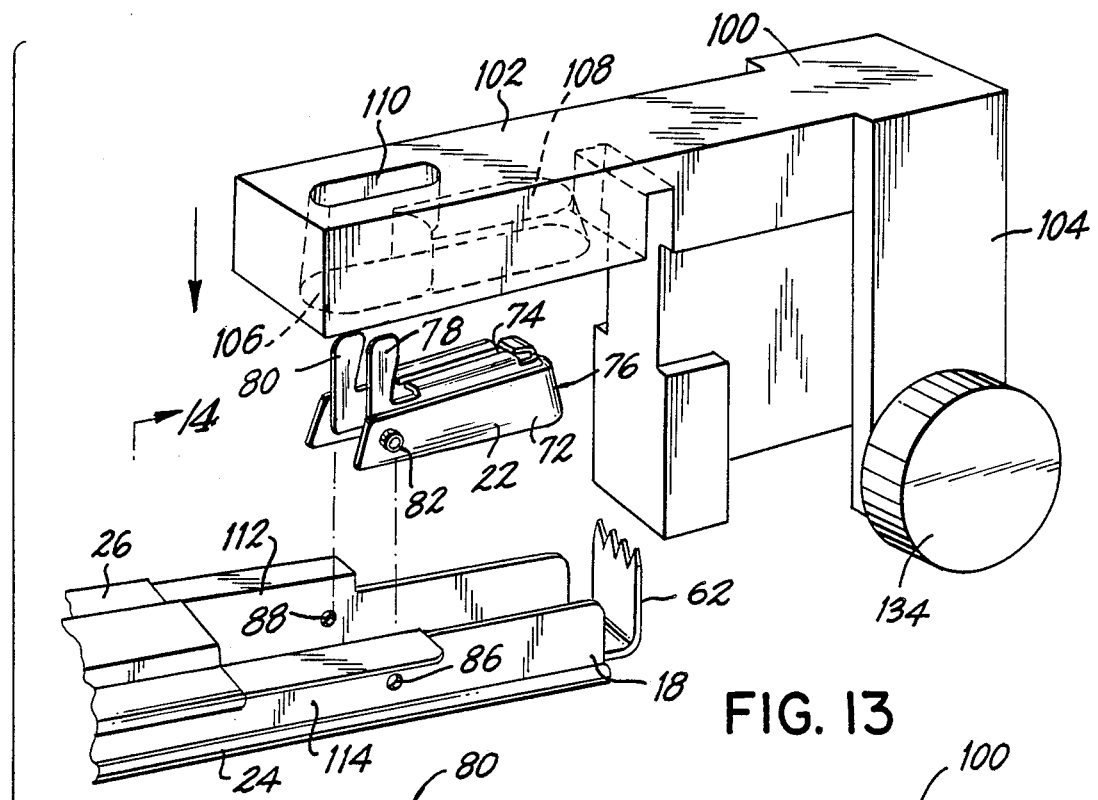
FIG. 13 is a perspective view of a blade assembly being inserted into an instrument with a jig in accordance with this invention.
Figure 15:
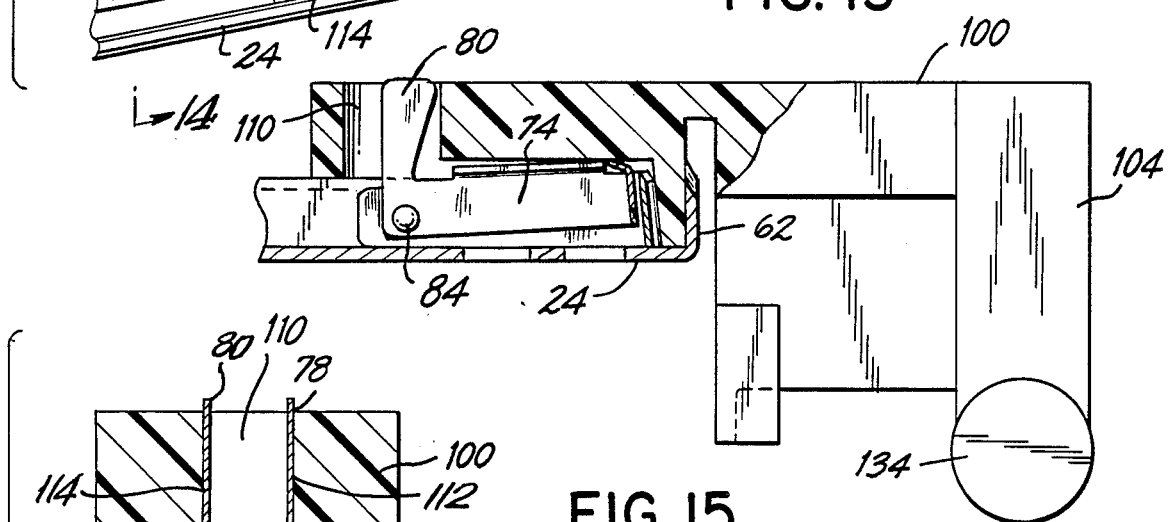
FIG. 15 is an inside sectional view of a new blade assembly being inserted into an instrument.
Figure 14:
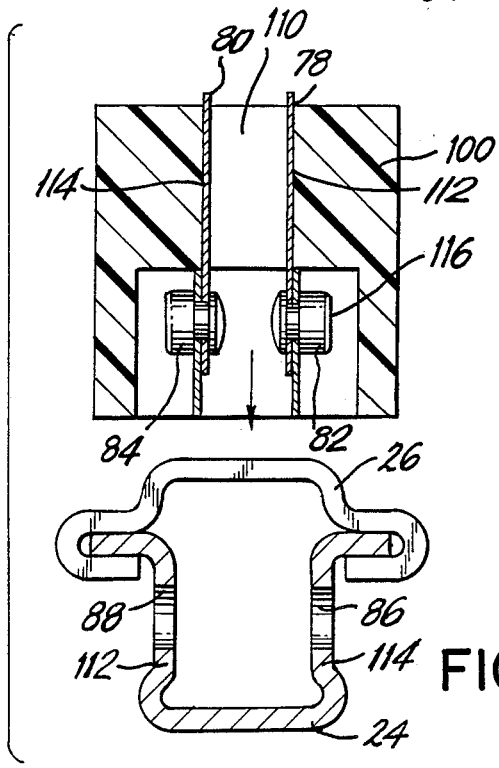
FIG. 14 is an end view of a blade assembly being placed into an instrument.
Figure 16:
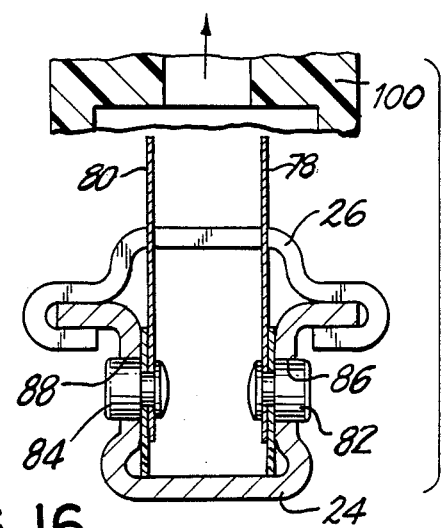
FIG. 16 is the jig being removed after a new blade assembly has been inserted into an instrument.

As shown in FIG. 13, prior to the insertion of a blade assembly, top component 26 is pulled back from cutting end 18. After the new blade 22 has been inserted into cavity 106, the jig is seated on bottom component 24, as shown in FIGS. 14 and 15, with the sidewalls 112, 114 of component 24 extending into cavity 106. As these sidewalls enter into the cavity, pins 82, 84 snap into holes 86 and 88 respectively. In order to facilitate the insertion of the pins into the holes, the pins may be slightly rounded as at 116. Once the pins are seated in the holes, the blade assembly is secured to component 24 and the jig 100 is lifted off as shown in FIG. 16.

As shown in FIG. 17, leg 104 comprises a platform 118, terminating in an upright extension 120. Extension 120 has a cutout 122. The leg also includes two opposed arms 124, 126 having facing bosses 128, 130 and outer disks 132, 134 as shown in FIG. 19. This section of the jig operates as follows. An instrument with an old blade assembly is placed on platform 118 with front wall 22 disposed in cutout 122 and the bosses 128, 130 in contact with the blade pins as shown in FIG. 19. The arms 124, 126 are slightly flexible. By squeezing outer disks 132, 134 together, bosses 128, 130 force pins 82, 84 out of their holes. Next the blade assembly may be removed from the instrument as shown in FIG. 20.

Obviously numerous modifications may be made to the invention without departing from its scope as defined in the appended claims.

What is claimed is:

1. A disposable blade assembly for a biopsy instrument comprising a first and a second blade pivotably joined to each other and cooperating to shear a sample from a tissue, each blade having a body;
    means for mounting said blades to the instrument;
    said body of each blade is U-shaped and includes two opposed side walls and a connecting wall;
    each said side wall of one of said blades includes a generally upright blade extension and a camming surface for controlling the movement of one of said blades with respect to the other blade.

2. The disposable blade assembly of claim 1 wherein said means for mounting said blades to the instrument includes two opposed pins disposed on said side walls of one of said blades for engaging a pair of holes in the instrument.

3. The disposable blade assembly of claim 1 wherein said first and second blades have first and second sets of walls respectively disposed in an opposed relationship to form a traveling shearing point between the blades as said second blade is pivoted from said first to said second position.

4. The disposable blade assembly of claim 3 wherein said first and second sets of walls are slanted to form said shearing point without other contact therebetween.

5. The disposable blade assembly of claim 3 wherein each set of walls comprises two side walls and a connecting wall extending therebetween, the side walls of said first set being slanted at a first angle and the side walls of said second set being slanted at a second angle larger than said first angle.

6. The disposable blade of claim 5 wherein said connecting wall of each set of walls is slanted.

7. The disposable blade assembly of claim 5 wherein the connecting wall of one of said sets has a notch for shearing.

8. The disposable blade assembly of claim 3 wherein one set of walls has an edge which is slanted for shearing.

9. A biopsy instrument for removing a sample tissue comprising:
    an elongated arm with a first and second end;
    a disposable blade assembly with a first and a second blade disposed at said first end, said first and second blades being removably attached to said arm and said second blade being pivotable between a first position wherein said blades are separated and a second position wherein said blades being engaged in a friction fit contact to generate a shearing force therebetween as said second blade pivots toward said second position;
    activating means at said second end for pivoting said second blade;
    a first and a second component included in said arm, said second component being slidable in a longitudinal direction with respect to said first component when engaged by said activating means;
    return means which cooperates with said second component to return said second blade from said second to said first position, said return means comprising a blade extension on said second blade and a slot on said second component for receiving said extension.

10. The instrument of claim 9 wherein said blades are U-shaped and are made of stainless steel.

11. The instrument of claim 9 wherein said activating means comprises a handle housing, a trigger element, and a resilient means attached to said housing and trigger element for urging said housing and trigger toward a rest position, said handle housing and trigger element cooperating to slide said second component in a first direction when said handle housing and trigger element are squeezed, and to slide said second component in a second direction when said handle housing and trigger element are returned to the rest position by said resilient means.

12. The instrument of claim 11 wherein said trigger element is pivotably attached to said housing, and said trigger element includes a trigger extension for engaging said second component.

13. The instrument of claim 12 wherein said trigger element is mounted on a pin and said resilient means is disposed on said pin.

14. The instrument of claim 13 wherein said resilient means comprises a torsion spring having a first trigger end engaging said housing and a second trigger end engaging said trigger element.

15. The biopsy instrument of claim 9 wherein said first and second blades have first and second sets of walls respectively disposed in an opposed relationship to form a traveling shearing point between the blades as said second blade is pivoted.

16. The biopsy instrument of claim, 15 wherein said first and second sets of walls are slanted to form said shearing point without other contact therebetween.

17. The instrument of claim 9 wherein one of said blades has two opposed mounting pins and said first component has two opposed holes for receiving said pins.

18. The instrument of claim 17 wherein said second blade has a camming surface, and said second component has a front face which cooperates with said camming surface to pivot said second blade from said first to said second position as said second component slides in a first direction.

* * * * *

UNITED STATES PATENT AND TRADEMARK OFFICE
CERTIFICATE OF CORRECTION

PATENT NO.    : 4,971,067
DATED         : November 20, 1990
INVENTOR(S)   : Bolduc, et al.

It is certified that error appears in the above-identified patent and that said Letters Patent is hereby corrected as shown below:

Column 2, line 45, delete "sides view of fixed blade" and substitute therefor --side view of a fixed blade--.

Column 3, line 42, delete "houncing" and substitute therefor --housing--.

Column 3, line 49, delete "closed Releasing" and substitute therefor --closed. Releasing--.

Column 3, line 53, delete "64 The" and substitute therefor --64. The--.

Column 5, line 42-43, delete "and outer disks 132, 134 as shown in" and substitute therefor --and shown in--.

Column 8, line 1, delete "claim, 15 wherein" and substitute therefor --claim 12 wherein--.

Signed and Sealed this

Twenty-fifth Day of August, 1992

Attest:

DOUGLAS B. COMER

*Attesting Officer*           *Acting Commissioner of Patents and Trademarks*